United States Patent [19]

Erickson

[11] 4,281,986

[45] Aug. 4, 1981

[54] DENTAL APPLIANCE

[76] Inventor: Norman R. Erickson, 1215 Felicita La., Escondido, Calif. 92025

[21] Appl. No.: 75,827

[22] Filed: Sep. 14, 1979

[51] Int. Cl.³ ............................................ A61C 17/04
[52] U.S. Cl. ..................................... 433/93; 433/136
[58] Field of Search ................................. 433/93, 136

[56] References Cited

U.S. PATENT DOCUMENTS

| 2,603,870 | 7/1952 | Nordin | 433/93 |
|---|---|---|---|
| 2,937,445 | 5/1960 | Erickson | 433/93 |
| 3,090,122 | 5/1963 | Erickson | 433/93 |
| 3,924,333 | 12/1975 | Erickson | 433/93 |
| 4,024,642 | 5/1977 | Zorovich | 433/93 |
| 4,192,071 | 3/1980 | Erickson | 433/93 |

*Primary Examiner*—Gene Mancene
*Assistant Examiner*—John J. Wilson
*Attorney, Agent, or Firm*—Charles C. Logan, II

[57] ABSTRACT

A dental appliance for evacuating debris and liquid from the mouth during dental operations having a collector member and a flexible collector membrane. The collector member has a semi-rigid bite block portion adapted to be gripped by the molars of the patient. The collector member also has a combination tongue guard and collector membrane holder formed integrally therewith and it has a first groove located with its open surface facing laterally to one side and a second groove located with its open surface facing laterally to the opposite side for detachably securing predetermined lateral edge surfaces of the collector membrane. The collector membrane is made of a flat sheet of polyethylene foam having a predetermined peripheral contour and it has a first groove engaging surface, a second groove engaging surface and a pair of tab members formed adjacent the opposite ends of the collector membrane. A pair of tab engaging slots are formed in the combination tongue guard and collector membrane holder for detachably engaging the tab members.

16 Claims, 8 Drawing Figures

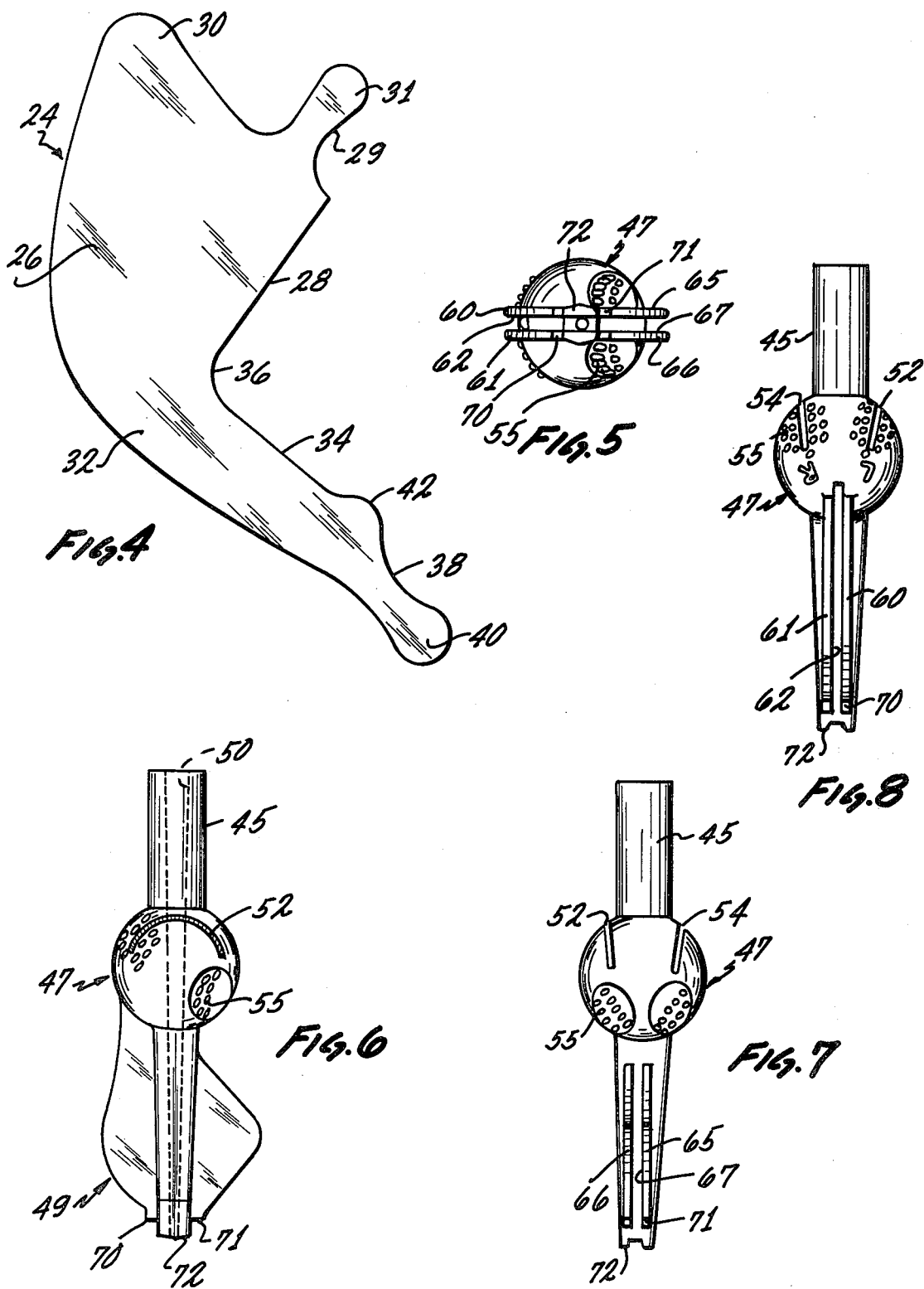

DENTAL APPLIANCE

BACKGROUND OF INVENTION

The invention relates to a dental appliance and more particularly to a device for collecting solid debris, for preventing debris from falling into the throat (oral pharynx) even when the patient is placed in a supine position, and removing liquid from the mouth of the patient during the conduct of dental operations therein.

In the past, saliva pumps (water pumps) have been used for removing liquid from the mouth of the patient during the conduct of dental operations. These pumps were perfected in the late 1900's and have for many years been a part of the dental operatory unit. In recent years a far more efficient system, the "high velocity vacuum" (an air pump) has been introduced to the dental profession. Although this system is highly efficient, it has several major drawbacks. First of all, the long life dependable system is very expensive. Secondly, the system is objectionable unless the air pump can be placed outside the confines of the dental office since it is very noisy and many medicaldental buildings do not lend themselves to this type of installation. Thirdly, until the advent of the Erickson Vac-Ejector described in U.S. Pat. No. 3,090,122, the use of high speed vacuum for evacuation required the service of a full time chairside assistant to hold the aspirator pipes. As a consequence of the three reasons recited above, only a relatively small percentage of dental operatories are equipped with a high velocity vacuum system and some of these are not in use, or are frequently not used because of noise, lack of help or mechanical failure.

By contrast, virtually every dental operatory in the world is equipped with a saliva pump. Even in the case of most modern and recently constructed dental facilities with custom made units, a saliva ejector line is present, connected to either a water or air pump.

The saliva pump with its attached saliva ejector is a very inefficient device. It is present in almost every operatory since it normally comes as part of the equipment at very little added cost and because it is better than nothing. The saliva pump is inefficient for dental evacuation because it moves only a relatively small volume of air or liquid per unit time, as contrasted with the air pump which uses a great volume of air to sweep up liquids which are near any orifice of the system's oral appliance or aspirator pipe.

Also in the case of the saliva pump, any or all orifices to the system's saliva ejector must be immersed in the liquid to be evacuated. If air can enter the system through any orifice, only air will be evacuated. If the orifice to the saliva ejector (where only one exists) is occluded, a very high vacuum is created which results in severe injury to tissues if tissue take up is the cause of occlusion. Consequently, for almost a hundred years, saliva ejectors to be used with the saliva pump have been designed with initial considerations toward eliminating tissue injury by using multiple orifices, rubber tips, slots for air relief, etc. Further progress was made by attempts to keep the tongue out of the area of operation by adding a tongue blade, curls of plastic tubing, and the like, all of which were helpful in improving a bad situation. A major drawback to these prior systems, however, was that evacuation was only partial and that the patient needed to be seated in a nearly upright position. When it came to the point of maintaining an absolutely dry field for placement of filling materials, fluoride treatments, plastic sealants and the like, the operator had to resort to using cotton rolls, gauze sponges, or the like.

Attempts have been made to devise an instrument which would overcome or compensate for the deficiencies of the saliva pump. The inventor himself began working on the problem in the early 1950's. His first solution was a device disclosed in U.S. Pat. No. 2,937,445 which unfortunately was limited in its function and subject to the same failures as were all the contemporary and earlier devices designed to be used with the saliva pump. In the late 1960's the inventor again turned his attention to the task of trying to create an appliance which would make the saliva pump a truly viable evacuating system. The results of these efforts is disclosed in U.S. Pat. No. 3,924,333. This dental appliance, although having merit, suffers from a design that is too complex, and it is subject to the many deficiencies all appliances used with the saliva pump have experienced to date.

The basic problem that all the inventors have been tackling since the saliva pump was "perfected" has been the removal of saliva. However, saliva is generated by all healthy humans. It is necessary for the health and comfort of all the tissues, hard and soft, of the oral cavity and pharynx. It has been the advent of the high speed drill and the washed field technique which relies on copious amounts of coolant and wash water to be introduced into the area that is being operated on, that has created a problem. Not only does the liquid and the solid debris splash and spray about on the sensitive tissue of the soft palate and oral pharynx, they join whatever saliva the patient generates to form an unconfined "stew" that is spread all over the oral cavity. When the patient is reclined the stew gravitates into the patient's throat. The present day saliva ejector is impotent to prevent this.

It is an object of the invention to provide a dental appliance having positive means for forming a reservoir in the patient's mouth for collection of all the coolant and wash water and for directing these liquids to the evacuating orifice of the saliva ejector.

It is also an object of the invention to provide a dental appliance that would allow the patient to swallow a portion of his saliva only, thus allowing the patient to remain more comfortable as a result of saliva keeping lubricated and moist the tissues of the throat.

It is a further object of the invention to provide a dental appliance having a positive structure to control the tongue whereby it is confined to a level below and apart from the lingual surfaces of the teeth that are to be maintained dry during operations requiring the various quadrants of the mouth to be absolutely dry.

It is a further object of the invention to provide a dental appliance having positive means for the collection of induced liquids by utilization of portions of the natural anatomy of the oral cavity never before considered in design.

It is an additional object of the invention to provide a dental appliance which does not allow the passage of the liquid and solid debris into the throat.

It is also a further object of the invention to provide a dental appliance with structure for retaining the collector membrane which requires no special adhesive, clamps, connectors or the like.

It is an additional object of the invention to provide a dental appliance having structure for holding the membrane in the proper relation with the anatomical tissues which it contacts to form a reservoir for the collection of fluids and saliva that are generated.

It is an additional object of the invention to provide a dental appliance having an extension of a single evacuation bore so that the connecting tube from the saliva pump or other vacuum source does not come in contact with the oral tissues of the patient.

It is an additional object of the invention to provide a dental appliance having a tongue guard that can be utilized without a change in its assembly so that it can be used either from the right side or the left side of the patient to isolate and evacuate slightly more than one half of the teeth of either the right or the left upper and lower arches.

It is also a further object of the invention to provide a dental appliance whose cost makes it acceptable as a disposable item after being used by only one patient.

SUMMARY OF THE INVENTION

The dental appliance is utilized for retaining debris and liquid from the mouth during a dental operation. The dental appliance operates in the following manner. The semirigid bite block portion of the appliance is fashioned so it may be used alternatively in either the right or left quadrants of the dental arches. When it is first placed between the teeth, for example, on the right side of the patient, impressions are made in the deformable bite block portion by the cusps of the teeth contacting it. The impressions made, function to hold the appliance stable. When the dental appliance is reversed to the opposite side, untouched surfaces on the bite block portion to be impressed by the tooth cusps of that side are presented because it is necessary to rotate the appliance in order that the tongue guard is placed in its proper relation to the opposite arch. In short, new and distinct bite tracks are presented automatically with proper placement of the tongue guard.

The combination tongue guard and collector membrane holder which is integral with the bite block portion contains a single bore which serves as the channel for evacuation of fluids. This bore is continuous through the bite block portion and the handle extension.

The collector membrane has three prime functions. Firstly, it is to provide a positive watertight seal with the soft tissues it is to contact. Secondly, it is to act as a collector of all liquid introduced and/or generated in the area of the dental operation and to channel these liquids to the reservoir. Thirdly, it is to retain all solid debris.

The materials used in the dental appliance components are both excellent insulating materials which gives them the property of being instantly the same temperature as the tissues they contact. Consequently, no tissue shock or patient reaction results. Polystyrene is eminently successful for the collector member. The material used for the collector membrane is polyethylene foam, a sealed cell foam with a waxy surface which is both feathery soft and feathery light. Because of its internal cell construction, it has the "body" to maintain or return to its original shape and form. It is also waterproof.

When the dental appliance is inserted into the patient's mouth, a portion of the collector membrane which extends outwardly from the combination tongue guard and collector membrane holder lies in sealing contact with the soft tissues overlying the mylohyoid line of the mandible. An adjacent portion of the membrane continues on a straight course for a short distance posteriorly and then curves upwardly in contact with the lingual mucosa of the ascending ramus. It continues the arc past and lingual to the maxillary tuberosity as it extends forward onto the hard palate. The breadth of the membrane extends across the palate and the throat to the opposite arch. The membrane has a slightly elevated span so that the spray and splash of liquids as they fall upon the tissues of the teeth, palate and collector membrane run together and course down the membrane to a point where the membrane lies about one centimeter below the level of the crest of the gingival tissues of the lower arch. There the arch and the lingual tissue cover of the ramus act as a dam to retain the fluids for evacuation. This reservoir is about a centimeter deep and two centimeters broad. The reservoir concept is a creation to compensate for the limitations of the saliva pump, which to function efficiently, must be presented with no opportunity to evacuate air instead of liquid. This invention gives the saliva pump no means to dissipate its efforts.

Applicant discovered that a dental appliance which places the collecting membrane below the level of the retromolar area and in contact with tissues which are essentially vertical in relation to the plane of the collector membrane create a reservoir which becomes the low point to which all fluids present and induced would drain regardless of whether the patient was nearly upright ot nearly supine. Also important is the fact that the action of the tongue when the patient swallows, causes the collector membrane to rise and fall only a few millimeters. Since the collector membrane lines essentially at a right angle to the tissue it contacts and slides upon, and since those tissues lie in an essentially flat plane, the tissue contact is not lost and the collection reservoir remains unimpaired in function.

During the time while liquids are being evacuated from the reservoir formed by the collector membrane and its tissue contact, saliva in the area of the tongue and throat serves to maintain those tissues in a lubricated and comfortable condition. Any excess saliva is swallowed by the patient, which exercise is made easy by pressure of the teeth on the bite block portion.

If the operation subsequently requires a "dry field" state as in the placement of filling material or if the operation entailed only a "dry field," it may proceed without change of armamentarium. The teeth of either the upper or lower quadrant may be washed and dried and a cotton roll placed to block Stenson's duct. The dry field can be maintained as long as necessary with the patient remaining comfortable. The tissues of the throat, in particular, remain as in the normal state, lubricated and moist.

During the course of any of the previously described dental procedures, solid debris, which is retained by the collector membrane, can be removed at any time with an aspirator pipe if it is available.

In addition to its function of collecting and evacuating liquids, collecting solid debris, isolating and maintaining a dry field, this appliance virtually assures that small instruments, extracted teeth dropped, cast fillings or crowns, pieces of debris such as old fillings, pieces of teeth, and the like, cannot be lost into the throat where they might be swallowed, or worse, aspirated.

DESCRIPTION OF THE DRAWINGS

FIG. 4 is a top plan view of the collector membrane;

FIG. 5 is a front elevation view of the combination tongue guard and collector membrane holder;

FIG. 6 is a top plan view of the combination tongue guard and collector membrane holder;

FIG. 7 is a side elevation view of the combination tongue guard and collector membrane holder;

FIG. 8 is an opposite side elevation view of the combination tongue guard and collector membrane holder.

DESCRIPTION OF THE PREFERRED EMBODIMENT

Figure 1:
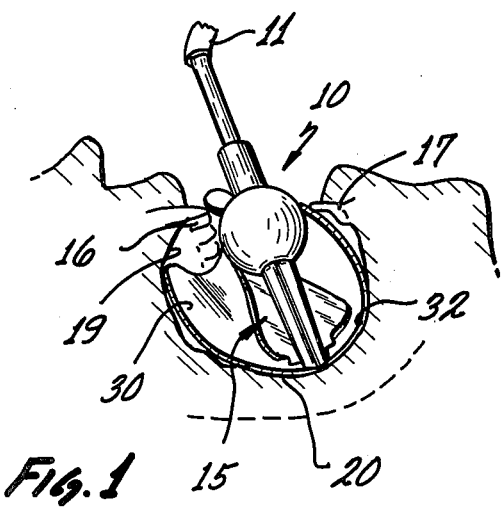
FIG. 1 is a longitudinal sectional view through a patient's mouth showing the dental appliance in place.
Figure 3:
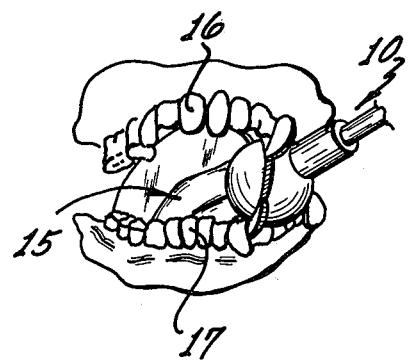
FIG. 3 is a top plan view of a patient's open mouth showing the dental appliance in place.
Figure 2:
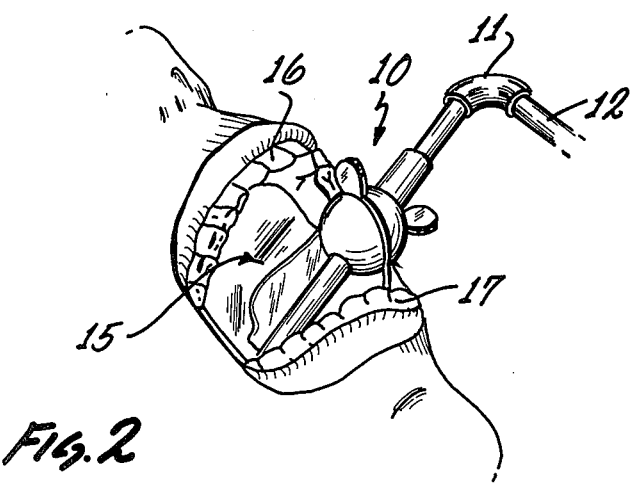
FIG. 2 is a perspective view of the open mouth of a patient showing the dental appliance in place.

The dental appliance is illustrated in FIGS. 1-3 in a patient's mouth. The dental appliance or collector member is generally designated numeral 10. It has an elbow member 11 attached to it and a connecting tube 12 in turn attached to the elbow member.

The patient's oral cavity 15 is shown with upper teeth 16 and lower teeth 17 and with the hard palate 19 inside the upper teeth. The ascending ramus of the mandible or jaw bone is designated numeral 20.

The structure of the collector member 10 is best described by referring to FIGS. 4-8. The collector membrane 24 has a main body portion 26 that has a major groove engaging surface 28 formed along one of its lateral edges and a palatal portion 30 is formed along its opposite side. Extending from one end of main body portion 26 is a neck portion 29 having a tab member 31 formed thereon. At the other end of the main body portion 26 is found a lingual portion 32 that extends laterally therefrom. Along one side of lingual portion 32 is formed the minor groove engaging surface 34. Along the edge surface of collector membrane 24 between the major groove engaging surface 28 and the minor groove engaging surface 34 is found the neck or distal extension engaging surface 36, major groove engaging surface 28, distal extension engaging surface 36, and minor groove engaging surface 34 of membrane 24 form a cut-out portion that shapes the membrane into a preformed cup configuration when it is assembled with the bite block portion 47 and combination tongue guard and collector membrane holder 49. At one end of lingual portion 32 is formed a neck portion 38 to which is attached a tab member 40. A protrusion 42 is formed along the edge of lingual portion 32.

The collector member 10 has an extension member portion 45, a bite block portion 47, and a combination tongue guard and collector membrane holder 49. A bore 50 extends throughout the length of the collector member.

The bite block portion 47 is substantially spherical in shape and it has a pair of tab engaging slots 52 and 54 formed in its outer surface. A plurality of bumps 55 are formed on the outer surface of bite block portion 47 in a predetermined pattern to aid the patient in biting into the bite block portion. The outer surface of bite block portion 47 also has raised letter designations identifying the two tab engaging slots for reasons to be stated later.

The combination tongue guard and collector membrane holder 49 is an elongated member having a pair of major lateral flanges 60 and 61 extending laterally outwardly therefrom to form major groove 62. Extending outwardly from the opposite lateral side are a pair of minor lateral flanges 65 and 66 that form minor groove 67 between them. At the free end of member 49 are a plurality of shoulders 70 and 71 and a neck portion or distal extension 72.

The manner in which the collector membrane 24 is connected to collector member 10 will now be described. Initially the major groove engaging surface 28 is placed within major groove 62 of the combination tongue guard and collector membrane holder 49. With the left thumb and forefinger holding collector membrane 24 in position, the right thumb and forefinger grasp tab 30 and draw it into and through either slot 52 or 54 of bite block portion 47. The material between the tab and the bulk of the collector membrane will elongate to form a thinner strip which slips into the slot while the tab projecting from the far end of the slot serves as a retainer because of its thickness. The tab is pulled into the slot marked (R) if you are going to work on the right side of the patient's mouth and it is pulled into the slot marked (L) if you are going to work on the patient's left side. Next the collector membrane is drawn around the distal extension 72 of the evacuation orifice and minor groove engaging surface 34 is inserted into minor groove 67. Tab 40 is then grasped and neck portion 38 is elongated by stretching so that it can be drawn into the other open slot of bite block portion 47. At this point the collector membrane 24 has been drawn into a cup shaped form. Now the collector membrane 24 is grasped at a point such that neck or distal extension engaging surface 36 can be gently drawn off the orifice projection of neck portion 72 and in a direction off center and the tension is released on the collector membrane 24. Neck or distal extension engaging edge surface 36 now is circumferentially engaging neck portion 72 along shoulders 70 and 71. The collector membrane now reassumes its cup shaped form leaving the evacuating orifice free of obstruction and a continuous rolled crease has been formed along the lateral edge of major flanges 60 and 61 from the tip of distal extension 72 to the bite block portion 47. This allows the film to adjust or be adjusted to variations in prominence of the tissues to be contacted.

Prior to inserting the dental appliance into the patient's mouth, the patient's lips and particularly the corners of the mouth should be lubricated with cocoa butter or vaseline. Polystyrene has a dry feel to the lips and a lubricant allows the corners of the mouth to be drawn over (to envelope) the bite block portion and contributes to patient comfort.

To place the dental appliance in the patient's mouth, it is held by extension member portion 45 and slid in over the lower arch. The orifice of the dental appliance is pressed inferiorly between tongue and mandible so that the line of the minor lateral flanges parallels the mylohoid line. The projection orifice 72 should be well below the gingival cuff of the second molar. In the same motion, the bite block portion 47 is pressed away from the side to be isolated and the flat mandibular bite surface is set onto the acclusal surface of the mandibular bicuspids and/or the first molar. With the forefinger of the free hand, distal extension 72 is pressed down a couple of millimeters away from the mandible. The patient is then asked to bite firmly enough to make a bite track in the bite block portion 47 and then told to relax. The bite track in bite block portion 47 will maintain the dental appliance in proper position while the patient exerts only an "at rest" pressure on bite block 47. Next the saliva ejector line is connected. The short curved vinyl connector 11 should be left in the rubber tulip of the saliva ejector line. It is necessary to make certain the saliva ejector is turned on before the open end is inserted into the dental appliance extension member 45 in order that the internal bore of the dental appliance is not contaminated. Next any needed adjustments to the collector membrane are made. The collector membrane is to form a soft contact with the tissue in an arc from distal extension 72 of the dental appliance anteriorly along the mylohyoid line to an arc of points just distal and lingual to the anterior border of the tissue covering the ascending ramus of the mandible. The arc continues up lingual to the tuberosity of the maxilla and anteriorly onto the hard palate.

What is claimed is:

1. A collector member having a semi-rigid bite block portion adapted to be deformed upon the initial bite of the patient so as to form a mold thereof for secure placement within a patient's mouth and which bite block portion resists further deformation permitting a patient to exert substantial pressure on said bite block portion:

a combination tongue guard and collector membrane holder connected to said bite block portion which is adapted to be captured within a patients mouth, said combination tongue guard and collector membrane holder having means on its sides for detachably securing predetermined lateral edge surfaces of a collector membrane thereto:

a flexible collector membrane that is substantially planar in its unassembled state having lateral edge surfaces, said collector membrane having laterally spaced first and second means for detachably securing said collector membrane to said bite block portion in order to pull said membrane into a preformed cup-shape configuration and to hold said membrane in such a configuration, said collector membrane having a cutout portion along its lateral edge between said first and second means for detachably securing said collector membrane to said bite block portion, said collector membrane in its assembled state having a preformed cup configuration produced by the lateral edges of said cut-out portion conforming to said means on the sides of said combination tongue guard and collector membrane holder, said membrane when in its assembled preformed cup configuration is adapted to be placed into its functional position within a patient's mouth to form a top of the mouth portion and a bottom of the mouth portion, the peripheral contour of the bottom of the mouth portion forms a sealing contact with the soft tissues overlying the mylohoid line of the mandible, and the lateral edges of the collector membrane where it is folded upwardly lies in sealing contact with tissue covering the internal walls of the ascending ramus of the mandible forming a reservoir for the collection of fluids and saliva generated, the top of the mouth portion of the collector membrane extends forwardly from the folded area over the palate where it conforms to and lies on the maxillary and palatal tissue thereby functioning to separate the mouth into a forward compartment that is being worked on and a rear compartment.

2. A collector member as recited in claim 1 wherein said bite block portion has a bore passing through it that communicates with a bore passing through said combination tongue guard and collector membrane holder, said collector membrane functioning during said dental operation to collect fluids and saliva generated and to divert them into and through the bores of said respective members.

3. A collector member as recited in claim 1 wherein said collector membrane is contoured to circumferentially seal the mouth of the patient into said forward and rear compartments.

4. A collector member as recited in claim 1 wherein said combination tongue guard and collector membrane holder is integrally formed with said bite block portion.

5. A collector member as recited in claim 1 further comprising an extension member that is connected to said bite block portion on a side opposite the side to which said combination tongue guard and collector membrane holder is connected.

6. A collector member as recited in claim 5 wherein said bore of said bite block portion also passes through said extension member.

7. A collector member as recited in claim 5 wherein said extension member is integrally formed with said bite block portion.

8. A collector member as recited in claim 1 wherein said collector membrane in its unassembled state has the form of a flat sheet of material.

9. A collector member as recited in claim 1 wherein said collector membrane is made from a material that gives it the characteristic properties of being stretchable in both the longitudinal and lateral directions.

10. A collector member as recited in claim 1 wherein said collector membrane is made of polyethylene foam.

11. A collector member as recited in claim 1 wherein said bite block portion is made of polystyrene material.

12. A collector member as recited in claim 1 wherein said means on the sides of said combination tongue guard and collector membrane holder for detachably securing predetermined lateral edge surfaces of a collector membrane thereto comprises a first groove located with its open surface facing laterally to one side and a second groove located with its open surface facing laterally to the opposite side.

13. A collector member as recited in claim 12 wherein the lateral edge surfaces on said collector membrane comprises a first groove engaging surface and a second groove engaging surface.

14. A collector member as recited in claim 1 wherein said means on said collector membrane for detachably securing said collector membrane to said bite block portion comprises a plurality of tab members formed on said collector membrane.

15. A collector member as recited in claim 14 further comprising means on said bite block portion for detachably engaging said tab members formed on said collector membrane.

16. A collector member as recited in claim 15 wherein said means on said bite block portion for detachably engaging said tab members comprises a plurality of tab engaging slots.

* * * * *